United States Patent [19]

Pistorius

[11] Patent Number: 4,518,537
[45] Date of Patent: May 21, 1985

[54] PROCESS FOR ISOLATING PARAFFINSULFONATE FROM THE REACTION MIXTURE OBTAINED ON SULFOXIDATING PARAFFINS

[75] Inventor: Rudolf Pistorius, Hünstetten, Fed. Rep. of Germany

[73] Assignee: Hoechst Aktiengesellschaft, Frankfurt, Fed. Rep. of Germany

[21] Appl. No.: 576,634

[22] Filed: Feb. 3, 1984

[30] Foreign Application Priority Data

Feb. 7, 1983 [DE] Fed. Rep. of Germany ....... 3304017

[51] Int. Cl.³ .............................................. C07C 139/00
[52] U.S. Cl. ............................ 260/504 R; 260/513 R; 204/162 SA; 204/162 HE
[58] Field of Search ....................... 260/513 R, 504 R; 204/162 SA, 162 HE

[56] References Cited

U.S. PATENT DOCUMENTS 3,577,456  5/1971  Kleiner ........................... 260/513 R
3,743,673  7/1973  Downer .......................... 260/513 R

FOREIGN PATENT DOCUMENTS 735096    4/1943   Fed. Rep. of Germany .
840093    9/1951   Fed. Rep. of Germany .
903815    9/1952   Fed. Rep. of Germany .
97053     1/1953   Fed. Rep. of Germany .
910165    1/1953   Fed. Rep. of Germany .
1139116  11/1962   Fed. Rep. of Germany .
1568591   3/1970   Fed. Rep. of Germany .
1910860  12/1972   Fed. Rep. of Germany .

Primary Examiner—Alan Siegel
Attorney, Agent, or Firm—Connolly and Hutz

[57] ABSTRACT

Process for isolating paraffinsulfonate from the extracts obtained on sulfoxidating n-paraffins by first of all separating off the bulk of the paraffin by adding alcohol at about 5°–55° C., then adding an amount of alkali required for neutralization in such a way that pH 7 is not undershot, separating off the precipitated alkali metal sulfate, distilling the alcohol out of the remaining paraffinsulfonate solutions, and concentrating the aqueous solution of the paraffinsulfonate by continuously introducing it into an evaporator in which the temperature should never drop below 130° C. from when the paraffinsulfonate solution is started to be introduced throughout the entire period for the evaporation of water.

3 Claims, No Drawings

PROCESS FOR ISOLATING PARAFFINSULFONATE FROM THE REACTION MIXTURE OBTAINED ON SULFOXIDATING PARAFFINS

The paraffinsulfonic acid solutions obtainable by sulfoxidating n-paraffins, for example by the process of German Pat. No. 910,165, contain, in addition to sulfur dioxide, about 20% strength aqueous sulfuric acid and hydrotropically dissolved paraffins. In order to isolate useful paraffinsulfonates from these reaction mixtures, it is necessary to remove sulfur dioxide, paraffins and sulfuric acid as completely as possible. There are a number of existing proposals for achieving this object, but only a few of them have proved to be technically and economically practicable.

In the process of German Pat. No. 1,910,860, for instance, the reaction mixture is first of all heated, to remove the bulk of the excess sulfur dioxide, and is then evaporated until the predominant portion of the now about 60% strength sulfuric acid separates from the mixture and forms a bottom phase. The alkanesulfonic acid is then neutralized, and the neutralized solution, which still contains all of the paraffin, is evaporated at relatively high temperatures, i.e. above about 240° C., during which a large proportion of the paraffin azeotropically evaporates as well. However, for the residual paraffin content in the end product to come down to a sufficiently small value (normally below 2% by weight), the product is stripped further by means of superheated steam.

With this procedure it has to be accepted, not least because of the high temperatures, that the product is relatively badly damaged, as indicated by its strong discoloration. It is consequently necessary to bleach with considerable amounts of hydrogen peroxide. However, to obtain a saleable product it is additionally necessary continuously to add, during the working-up process, phosphorus-containing products, for example phosphoric acid, as stabilizers. Although this process produces a product of acceptable color, it also has a phosphate content, albeit small, which is increasingly regarded as a disadvantage. The relatively high residual salt content, greater than 5% of alkali metal sulfate (based on the active detergent), and the clearly noticeable, peculiar odor of the product are similarly regarded as disadvantages.

By contrast, phosphate-free products having residual salt contents below 5% (based on the active detergent) are obtained by the process described in German Offenlegungsschrift 1,568,591, where the bulk of the paraffin is separated off by means of lower alcohols, as also already proposed in German Pat. Nos. 907,053 and 910,165, and the acid alcoholic solution is then neutralized by adding concentrated alkali metal hydroxide solutions at temperatures above 35° C. The precipitated alkali metal sulfate is filtered off, the remaining paraffin is then extracted with low-boiling hydrocarbons, and the solutions are then thickened to the desired final concentration.

It is true that this process variant precipitates sodium sulfate in readily filtered form, i.e. in a relatively coarse form, but, on the other hand, a relatively large amount of paraffin and paraffinsulfonate are co-precipitated at the same time and cannot, despite subsequent washing with further alcohol, be forced below, taken together, about 2% by weight of the dry alkali metal sulfate separated off. Furthermore, the required use of a low-boiling hydrocarbon for removing the paraffin residues complicates the process very much. The continuous thickening of the alkanesulfonate solutions to turn them into pastes having an active ingredient content of greater than 50% active detergent is likewise technically very difficult to carry out, because as the product becomes thicker it becomes more and more viscous, nor do the products obtained in this way meet the stated requirements in respect of odor.

It has now been found, surprisingly, that there is a technically very simple way of obtaining products which meet all the requirements, i.e. which are low in alkali metal sulfate, which are free of phosphate, which are light-colored and which are very low in odor, if the process proposed below is followed.

The invention provides a process for isolating paraffinsulfonate from the extracts which are obtained on sulfoxidating n-paraffins and from which the bulk of the paraffin has been separated by adding alcohol, which comprises neutralizing the alcoholic paraffinsulfonic acid solutions thus obtained with alkali metal hydroxides in such a way as not to drop below pH 7, and continuously concentrating in a preheated evaporator at at least 130° C., the paraffinsulfonate solution obtained on separating off the precipitated alkali metal sulfate.

The starting material for the process of the present invention can be the extracts from any sulfoxidation process. For example, it is possible to use the extracts obtainable by the processes of German Pat. Nos. 735,096, 840,093 or 903,815. It is furthermore also possible to start from extracts of the type obtained in the sulfoxidation by means of peroxides, ozone or γ-rays, for example as in the process of German Pat. No. 1,139,116. These extracts often have a high paraffindisulfonic acid content, which, however, does not interfere in the process of the present invention. The present process is preferably carried out with the aqueous extracts obtained on sulfoxidating n-paraffins having chain lengths of about 7 to about 18, preferably 10 to 18, carbon atoms. The extract is that clear solution which is obtained after the sulfoxidation when undissolved paraffin has been separated off. This extract can additionally also be heated to 80° to 105° C. before the alcohol is added. The effect achieved is a preseparation of about 20 to 33% by weight of the total amount of sulfuric acid present in the extract. As a result, the amount of alkali metal hydroxide necessary for the subsequent neutralization is reduced, and less water needs to be evaporated off at the end of the process.

The low-molecular alcohols used for separating off the paraffin, such as methanol, ethanol and isopropanol, preferably methanol and ethanol, but in particular methanol, should be added to the extract in an amount of 50 to 500, preferably 100 to 200, parts by weight, based on 100 parts by weight of paraffinsulfonic acids. The most suitable amount varies with the particular composition of the extract. It has been found to be advantageous to add to the extract at least sufficient alcohol to separate off at least 70%, preferably 80–95%, of the paraffin present. On the other hand, the amount of alcohol required for a desired degree of paraffin elimination can be the lower the more (dilute) sulfuric acid is removed by heating the reaction mixture to 80° to 105° C. and then separating off the bottom phase before the alcohol is added.

Again depending on the composition of the reaction mixture and the amount of alcohol, it can be advantageous partially to preneutralize the extract even before the alcohol is added, i.e. to add even before the alcohol is added about 5 to 50%, but in particular 10 to 30%, of the amount of alkali which is required for complete neutralization. However, the amount of alkali added before the alcohol is added must not be so high as to cause alkali metal sulfate to precipitate when the chosen amount of alcohol is added, since the alkali metal sulfate and the precipitated paraffin will otherwise form a suspension which will be difficult to separate again.

The precipitation of paraffin by adding alcohol should be carried out at 5° to 55° C., advantageously at 15° to 40° C., but preferably at 18° to 30° C., and the mixture should be allowed at least 5 minutes, but at most 90 minutes, preferably 8 to 20 minutes, to separate.

The reaction mixture thus freed from the bulk of the paraffin is immediately thereafter neutralized at 10° to 80° C., preferably at 40° to 70° C., by simultaneously pouring together with thorough stirring, the alkali and the alcoholic paraffinsulfonic acid solution at a metering rate so adjusted that the pH, measured with a calibrated pH electrode in the mixture of the two liquids, is always above 7, in particular above 11.0, and, depending on the conditions of the further working-up, the pH is adjusted at the end of the neutralization to between 10 and 12, so that the end product has a neutral to weakly alkaline pH.

Any desired alkali can be used to neutralize the paraffinsulfonic acids. It is possible to use sodium hydroxide or potassium hydroxide, advantageously in the form of concentrated aqueous solutions, but it is also possible to use sodium carbonate, potassium carbonate, sodium bicarbonate or potassium bicarbonate.

At the end of the neutralization, the temperature is lowered to 10° to 65° C., advantageously to 20° to 40° C., in order to complete the precipitation of the alkali metal sulfate, and the paraffinsulfonate solution is freed from the relatively finely divided sodium sulfate by decanting or centrifuging.

The alcohol-moist alkali metal sulfate, still with adherent paraffinsulfonate and paraffin, can be, for example, advantageously suspended in a further alcohol, and can now be filtered off very easily and cleanly, and be additionally washed, if required, so that, in total, less than 2%, but in particular less than 1%, of paraffinsulfonate and paraffin, based on the amount of alkali metal sulfate, are discharged together with the alkali metal sulfate. The suspension and wash alcohol can be reused unchanged for a renewed separation of paraffin without the need for any separate working-up.

The paraffinsulfonate solution thus obtained is then evaporated, initially until all the alcohol is removed. The paraffinsulfonate solution is evaporated further by slowly introducing it into an evaporator which has already been preheated to a temperature of at least 130°. The addition of the paraffinsulfonate solution into the evaporator is controlled at such a rate that this temperature of 130° C. is never undershot. The most suitable temperature for this concentrating step is between 130° and 200° C., preferably between 135° and 180° C. This temperature depends on the distribution of the chain length in the alkyl groups of the paraffinsulfonate. In the course of this evaporation, the result of which is a relatively highly mobile melt, the bulk-as a rule 70–95%-of the paraffin still present in the paraffinsulfonate passes over azeotropically. If necessary, the last traces of paraffin can finally be removed by further stripping with a little superheated steam at bottom temperatures of 130° to 200° C., in particular at 150° to 180° C. If the paraffinsulfonate solution is concentrated in the manner described, the product obtained on cooling the melt is up to 95% pure paraffinsulfonate. By contrast, the process described in German Pat. No. 1,568,591 gives products which are only at most 50% pure. The highly concentrated paraffinsulfonate of the present process can then be adjusted to any desired concentration by adding water, at 90° to 150° C., to which 0.01 to 0.9, in particular 0.2 to 0.5, % of $H_2O_2$ can be admixed to remove last traces of odor. The advantages of the process according to the invention should be seen in the fact that the paraffinsulfonate is much less odorous and that less paraffin and paraffinsulfonate adhere to the alkali metal sulfate separated off, so that the loss of these products is less. In addition, compared with the process described in German Pat. No. 1,568,591, there is no need for additional extractant, and, what is more, the paraffinsulfonate is obtained in a very much higher concentration.

EXAMPLE 1

In a sulfoxidation apparatus, straight-chain paraffin hydrocarbons having 12 to 18 carbon atoms were reacted at 30° to 40° C. with sulfur dioxide and oxygen in the presence of water and under irradiation with UV light. This gave an aqueous extract which was freed from sulfur dioxide by heating under a slight vacuum to 85° C. Thereafter the extract consisted of 36.4% of water, 8.2% of sulfuric acid, 23.1% of sulfonic acids and 32.3% of paraffins. 2,433 g of this degassed extract were cooled down to such an extent that mixing with 973 g of methanol produced a temperature of 25° C. In the course of 15 minutes, 735 g of paraffin separate off as a shiny colorless top layer. By simultaneously passing in at 65° C. the extract freed from the bulk of the paraffin as well as 480 g of 50% strength sodium hydroxide solution, the mixture was neutralized in such a way that the pH did not drop below 11 (measured with a calibrated glass electrode). The mixture was brought to pH 10.8 at the end of the neutralization. The neutralized mixture was then cooled down to 30° C., and the sodium sulfate was filtered off on a pressure filter. The sodium sulfate cake was washed three times with 30 g of methanol each time. The dried sodium sulfate weighed 290 g and still contained 0.6 g of water, 2.5 g of alkanesulfonate and 0.8 g of paraffin.

The neutralized solution freed from sodium sulfate (2,972 g) was evaporated under atmospheric pressure up to a top temperature of 90° C., 984 g of distillate passing over with 3 g of paraffin floating on top. This concentrate was continuously metered into a heated flask at 150° C.–160° C. (bottom temperature), 1,139 g of water passing over together with 41 g of paraffin. It was possible to drive a further 3 g of paraffin out of the melt, maintained at 160° C., by stripping with 50 g of superheated steam at 180° C.

Adding 375 g of water and 3 g of hydrogen peroxide at 90° to 100° C. gives 1,000 g of a 60% strength paraffinsulfonate paste which still contains 0.97% of sodium sulfate and 0.8% of paraffin and which is virtually colorless and odorless.

EXAMPLE 2

Use was made of the same degassed extract as in Example 1, but 2,433 g thereof were preneutralized with 100 g of 50% strength sodium hydroxide solution before the methanol was added. Under identical conditions as in Example 1, however, 740 g of paraffin separate off as top phase. The remaining working-up was analogous to Example 1, i.e. complete neutralization required a further 380 g of 50% strength sodium hydroxide solution and on evaporating the melt, 1,140 g of water passed over together with 39 g of paraffin-the end product (998 g) still contains 0.5% of paraffin and 0.9% of sodium sulfate and is virtually colorless and odorless.

EXAMPLE 3

2,433 g of the same degassed extract described in Example 1 were heated to 90° C. and allowed to settle for 6 minutes, during which 285.6 g of 20.5% strength sulfuric acid which also contained 0.6% of alkanesulfonic acids were separated off as the bottom phase. 860 g of methanol were added under the same conditions as in Example 1, whereupon it was possible, after 15 minutes, to separate off 741 g of paraffin as the upper phase. Thereon, the mixture was neutralized with 365 g of 50% strength sodium hydroxide solution likewise under the same conditions as in Example 1. When the neutralized mixture had cooled down to 30° C., a pressure filter was used to separate off the precipitated sodium sulfate (187 g) which after 3 washes with 20 ml of methanol each wash and after 3 hours' drying at 85° C. still contained 0.5 g of water, 2.7 g of alkanesulfonate and 0.7 g of paraffin. The neutralized solution freed from sodium sulfate (2,330 g) was evaporated under atmospheric pressure up to a top temperature of 90° C., 862 g of distillate passing over with 5 g of paraffin floating on top. This concentrate was continuously metered into a heated flask at 150°–160° C. (bottom temperature), 765 g of water passing over together with 34 g of paraffin. It was possible to drive a further 10 g of paraffin out of the melt, maintained at 160° C., by stripping with 300 g of superheated steam at 180° C.

Adding 410 g of water and 3 g of hydrogen peroxide at 90° to 100° C. gives 1,000 g of a 60% strength paraffinsulfonate paste which still contains 0.6% of sodium sulfate and 1.6% of paraffin and which is virtually colorless and odorless.

I claim:

1. A process for isolating paraffinsulfonate from the extracts which are obtained on sulfoxidating n-paraffins and from which the bulk of the paraffin has been separated by adding alcohol, which comprises neutralizing the alcoholic paraffinsulfonic acid solutions thus obtained with alkali metal hydroxides in such a way as not to drop below pH 7, and continuously concentrating in a preheated evaporator at at least 130° C., the paraffinsulfonate solution obtained on separating off the precipitated alkali metal sulfate.

2. The process as claimed in claim 1, wherein 5 to 50% of the total amount of alkali necessary for the neutralization is added to the extract before the alcohol is added.

3. The process as claimed in claim 1, wherein the alcoholic paraffinsulfonic acid solution was obtained by:
   (a) reacting paraffin hydrocarbons with sulfur dioxide and oxygen in the presence of water and under irradiation with ultraviolet light, in a reaction medium,
   (b) removing sulfur dioxide by heating, and
   (c) adding the alcohol to the resulting degassed medium, thereby obtaining the alcoholic paraffin sulfonic acid solution, unreacted paraffin separating off as a top layer of the said medium.

* * * * *